(12) United States Patent
Havens et al.

(10) Patent No.: US 7,466,133 B2
(45) Date of Patent: Dec. 16, 2008

(54) SYSTEMS, METHODS AND APPARATUS OF A MAGNETIC RESONANCE IMAGING SYSTEM TO PRODUCE A STRAY FIELD SUITABLE FOR INTERVENTIONAL USE

(75) Inventors: Timothy John Havens, Florence, SC (US); Stephen R. Elgin, Florence, SC (US); Ricardo Becerra, Waukesha, WI (US)

(73) Assignee: General Electric Company, Schenectady, NY (US)

(*) Notice: Subject to any disclaimer, the term of this patent is extended or adjusted under 35 U.S.C. 154(b) by 536 days.

(21) Appl. No.: 11/069,294

(22) Filed: Mar. 1, 2005

(65) Prior Publication Data

US 2006/0238196 A1    Oct. 26, 2006

(51) Int. Cl.
*G01V 3/00* (2006.01)

(52) U.S. Cl. ........................... 324/319; 335/216
(58) Field of Classification Search ............... 324/319, 324/320; 335/216
See application file for complete search history.

(56) References Cited

U.S. PATENT DOCUMENTS

| | | | |
|---|---|---|---|
| 4,682,134 A | 7/1987 | Laskaris | |
| 4,924,186 A | 5/1990 | Kawamoto et al. | |
| 5,304,934 A | 4/1994 | Laskaris | |
| 5,307,039 A | 4/1994 | Chari | |
| 5,416,415 A | 5/1995 | Dorri | |
| 5,646,532 A | 7/1997 | Knuttel et al. | |
| 5,721,523 A * | 2/1998 | Dorri et al. | 335/216 |
| 5,801,609 A * | 9/1998 | Laskaris et al. | 335/216 |
| 6,064,290 A | 5/2000 | Xu et al. | |
| 6,140,900 A | 10/2000 | Crozier | |
| 6,255,929 B1 | 7/2001 | Xu et al. | |
| 7,109,708 B2 * | 9/2006 | Havens | 324/307 |

FOREIGN PATENT DOCUMENTS

EP      1 074 852 A2    7/2001
WO   WO 2004/097443 A1   11/2004

OTHER PUBLICATIONS

Forbes & Crozier, Novel Target-Field Method for Designing Shielded Biplanar Shim and Gradient Coils, IEEE:Transactions on Magnetics,Jul. 2004,pp. 1929-1938,vol. 40,No. 4, US.

Brideson et al., Winding Patterns for Actively Shielded Coils with Asymmetric Target-Fields,Measurement Science and Technology,2003,pp. 484-493,vol. 14, UK.

Forbes & Crozier, "Novel Target-Field Method for Designing Shielded Biplanar Shim and Gradient Coils", IEEE Transactions on Magnetics, 2004, vol. 40, No. 4, pp. 1929-1938, see figures 6 and 9.

* cited by examiner

*Primary Examiner*—Louis M Arana
(74) *Attorney, Agent, or Firm*—Michael G. Smith, Esq.; Peter Vogel, Esq.; Jean Tibbetts, Esq.

(57) ABSTRACT

Systems, methods and apparatus are provided through which in some embodiments a magnetic resonance imaging (MRI) system includes one or more magnetic shield coils positioned asymmetrically in the casing and also positioned in close proximity to one of two apertures of an inner bore of the MRI system. In those embodiments, the position of the one or more magnetic shield coils provides an asymmetric magnetic stray field during operation of the MRI system, which in turn allows operation of electronic medical diagnostic equipment or electronic medical monitoring equipment in close proximity to the MRI.

22 Claims, 9 Drawing Sheets

SYSTEMS, METHODS AND APPARATUS OF A MAGNETIC RESONANCE IMAGING SYSTEM TO PRODUCE A STRAY FIELD SUITABLE FOR INTERVENTIONAL USE

FIELD OF THE INVENTION

This invention relates generally to magnetic resonance imaging systems, and more particularly to magnetic resonance imaging systems for interventional imaging.

BACKGROUND OF THE INVENTION

Interventional imaging is the use of magnetic resonance imaging (MRI) of a subject during remedial action upon the subject. MR images are used to monitor the progress, success and problems that occur during the remedial action.

Interventional medical imaging is the practice of MRI of a patient during medical treatment of the patient to monitor the progress, success and problems that occur during the medical treatment. Interventional imaging is used in emergency and non-emergency situations. Examples of non-emergency interventional imaging include MRI-guided biopsy, MRI-guided surgery, dynamic musculoskeletal MRI, MRI-guided minimally invasive thermal therapies, MRI-guided vascular interventions, and fluoroscopy.

In interventional imaging, the MR image is generated continuously, or intermittently at regular or irregular intervals, or on an ad-hoc basis.

However, medical interventional imaging often requires the use of surgical equipment. The surgical equipment includes electronic medical diagnostic equipment or electronic medical monitoring equipment, such as a surgical microscope and patient monitoring equipment. However, the strong magnetic stray field of a MRI system often interferes with the operation of the additional equipment within a certain range of the MRI system. Surgical equipment is operated outside of the range. In one example an MRI system must not generate a magnetic field above five gauss beyond a range of four meters from the center of an MRI magnet of the MRI system in order to accommodate operation of other electrical medical equipment 4 meters from the MRI system.

Operating the surgical equipment outside of the range of electromagnetic interference of an MRI system is at the very least, inconvenient for the technicians and healthcare providers involved in the use of the additional equipment. The inconvenience results in a loss of productivity of the technicians and healthcare providers. In more serious situations, the inconvenience can yield poor communication between the technicians and healthcare providers that can result in less than optimal healthcare for the patient.

More specifically, conventional interventional MRI systems comprise two basic types of systems, open MRI systems with interventional access and cylindrical MRI systems with movement of patient.

In regards to open MRI systems with interventional access, the open MRI systems typically have lower magnetic stray field with lower imaging capability. This type of MRI system allows real-time intervention at some limited surgeon access. Other open MRI systems have higher magnetic stray field strength and increased access, but these systems also have larger stray fields. The larger stray field limits access by technicians and healthcare providers to required surgical equipment such as microscopes, patient monitoring equipment, etc.

In regards to cylindrical systems with movement of patient, these systems can be used for interventional procedures by removing patients from high magnetic stray field region for surgery and replacing patient in cylindrical system to verify interventional procedures. However this presently requires motion of the patient by a considerable distance to move patient to a region of low magnetic stray field strength. In the conventional cylindrical MRI systems, the 5 gauss line is located 4 meters from magnet isocenter along the patient axis. Thus, moving the patient to a region of low magnetic stray field strength typically requires motion of table away from the system and increases possibility of registration and/or misalignment of patient with imaging system.

In general, cylindrical MRI systems are more attractive for their higher imaging capability, inherent high signal to noise ratio imaging speed and wide range of pulse sequences available. Cylindrical systems can be used for interventional procedures by inserting catheters while the patient is out of the magnet, then manipulating the catheters while the patient is in magnet. However, again the high field region extends a considerable distance from the magnet, with 5 Gauss regions typically 4 meters axially and 2.5 meters radially. This limits placement of some equipment in close to the magnet.

An increasingly popular technique used in interventional procedures, is imaging fusion. Imaging fusion is a combined use of MR and X-ray imaging. Since these two imaging systems are typically installed in separate rooms, the patient has to be transported significant distance increasing the chance for mis-registration and the time for the procedure. Today, most hospitals that are using high field cylindrical magnet MRI systems for surgery, either to perform the imaging and surgery in separate rooms, requiring significant patient travel, or to perform the imaging and surgery in a very large room to allow the patient to be moved to a region outside the 5 Gauss field, where standard surgery equipment and tools can be operated.

For the reasons stated above, and for other reasons stated below which will become apparent to those skilled in the art upon reading and understanding the present specification, there is a need in the art to place and operate interventional medical equipment such as electronic medical diagnostic equipment or electronic medical monitoring equipment in close proximity to a MRI system.

BRIEF DESCRIPTION OF THE INVENTION

The above-mentioned shortcomings, disadvantages and problems are addressed herein, which will be understood by reading and studying the following specification.

In one aspect, a MRI system includes one or more magnetic shield coils that are positioned asymmetrically in the casing and also positioned in close proximity to one of two apertures of an inner bore of the MRI system. The position of the one or more magnetic shield coils provide an asymmetric magnetic stray field during operation of the MRI system, which in turn provides a magnetic stray field of which electronic medical diagnostic equipment or electronic medical monitoring equipment can be operated in close proximity to the MRI. Thus, the MRI system solves the need in the art to operate interventional medical equipment in close proximity to the MRI system.

In another aspect, an MRI system has no outer diameter shield coil in an outer portion from the narrower diameter portion of a stepped bore.

In yet another aspect, an MRI system has a shield coil positioned along the inner diameter of the casing and a bore of a continuous diameter.

In still another aspect, an MRI system has a magnetic shield coil positioned between the inner diameter and the outer diameter of a casing.

In a further aspect, an MRI system has a magnetic shield coil positioned between the inner diameter and the outer diameter of a flared casing.

In yet a further aspect, an MRI system generates an image from electromagnetic resonance induced by a magnet with an asymmetric stray field according to an embodiment.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, apparatus of embodiments are described. In the third section, methods of embodiments are described. In the fourth section, the hardware and the operating environment in conjunction with which embodiments may be practiced are described. Finally, in the fifth section, a conclusion of the detailed description is provided.

System Level Overview

Figure 1:
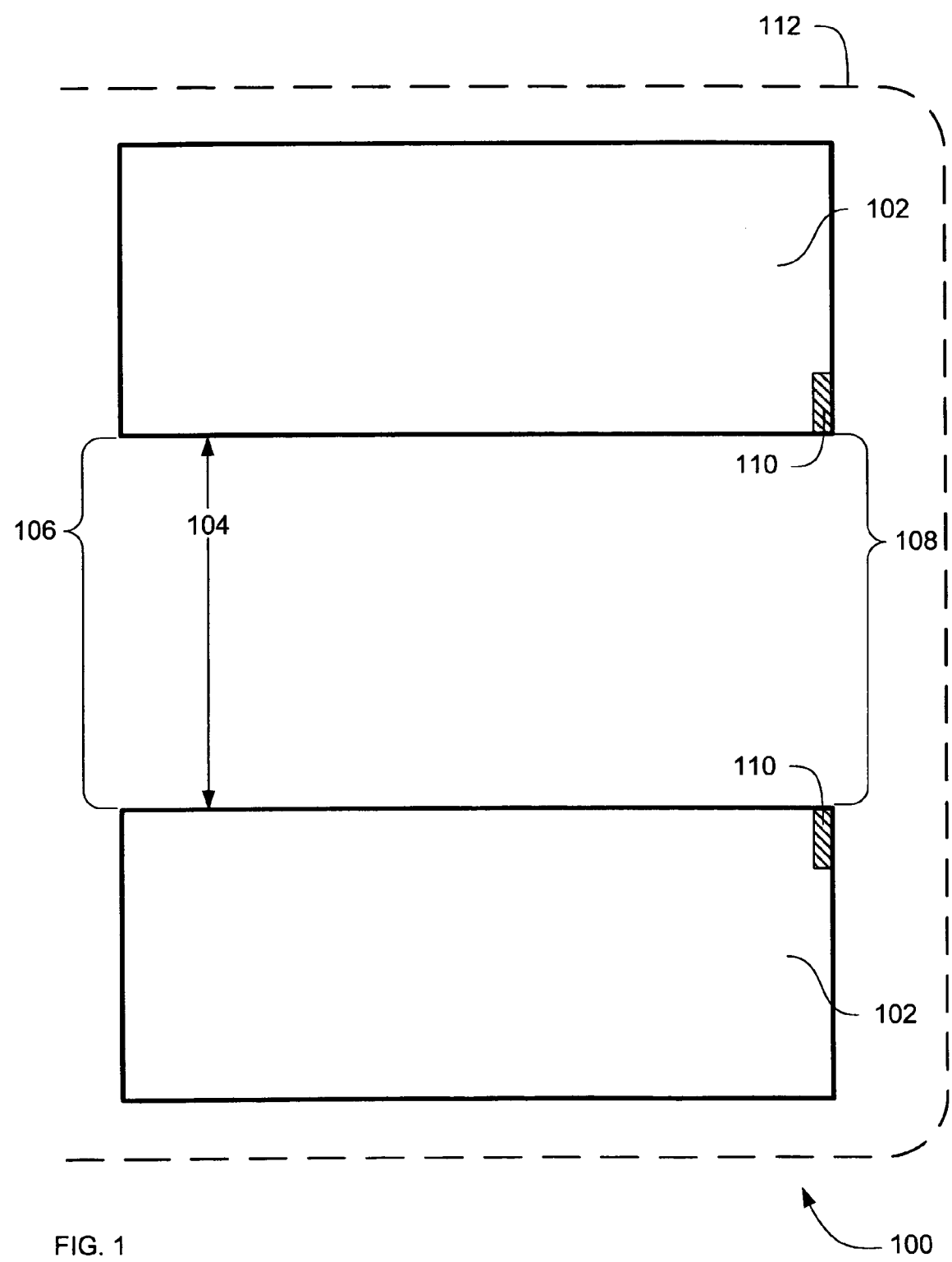
FIG. 1 is a block diagram that provides a system level overview of a magnetic resonance imaging system to provide access in close proximity.

FIG. 1 is a block diagram that provides a system level overview of a magnetic resonance imaging system to provide access in close proximity. System 100 solves the need in the art to place additional electronic medical diagnostic equipment or electronic medical monitoring equipment in close proximity to an MRI system.

System 100 includes a casing 102 having an inner bore 104. The inner bore 104 defines an inner diameter of the casing and has two apertures 106 and 108.

System 100 also includes one or more magnetic shield coils 110. The one or more magnetic shield coils 110 are positioned asymmetrically in the casing 102. The one or more magnetic shield coils 110 are also positioned in close proximity to one of the two apertures 106 and 108. Furthermore, the one or more magnetic shield coils 110 are positioned in close proximity to the inner bore 104. As a result, the asymmetric position of the one or more magnetic shield coils 110 provide an asymmetric magnetic stray field 112 during operation of the system 100. The asymmetric magnetic stray field 112 provides a magnetic stray field that in which electronic medical diagnostic equipment or electronic medical monitoring equipment is operable in close proximity to the system 100 on the side of the system in which the asymmetric magnetic stray field 112 does not extend far from the system 100.

In some embodiments the 5 gauss line of the asymmetric magnetic stray field 112 extends a mere 0.5 meters from the side of the system. Such close proximity of 0.5 meters provides for a magnetic field beyond which electrical equipment is operable. Thus, system 100 solves the need in the art to place interventional electronic medical diagnostic equipment or electronic medical monitoring equipment in close proximity to system 100. Accordingly, system 100 supports operational interventional medical imaging.

In FIG. 1, the proportional distance of asymmetric magnetic stray field 112 to apparatus 100 is depicted disproportionately close to apparatus 100.

A system level overview of the operation of an embodiment has been described in this section of the detailed description. While the system 100 is not limited to any particular casing 102, inner bore 104, apertures 106 and 108, magnetic shield coil 110, and asymmetric magnetic stray field 112, for sake of clarity a simplified casing 102, inner bore 104, apertures 106 and 108, magnetic shield coil 110, and asymmetric magnetic stray field 112 have been described.

Apparatus of an Embodiment

In the previous section, a system level overview of the operation of an embodiment was described. In this section, the particular apparatus of such an embodiment are described by reference to a series of diagrams.

Figure 2:
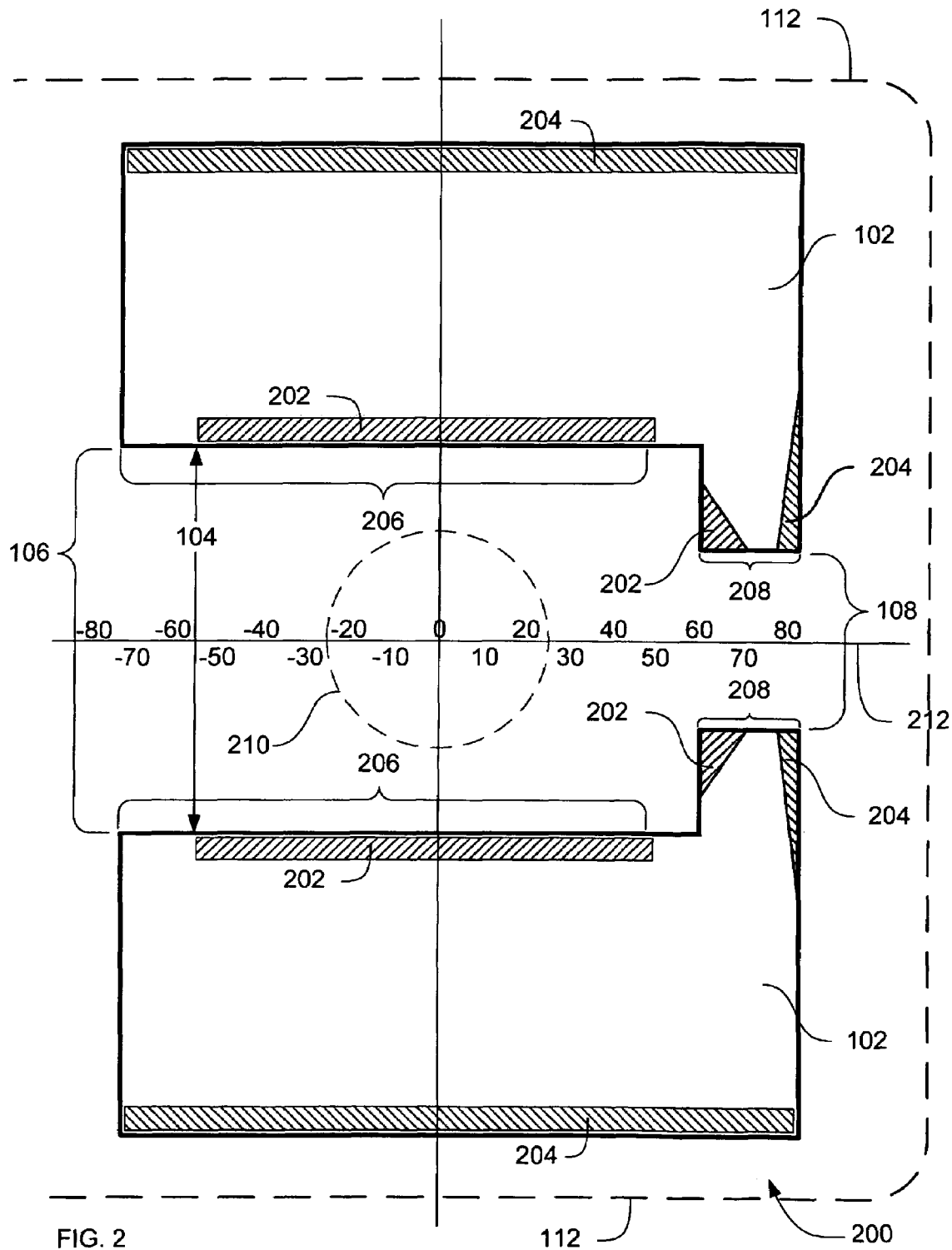
FIG. 2 is a longitudinal cross-section diagram of an apparatus to provide access in close proximity according to an embodiment.

FIG. 2 is a longitudinal cross-section diagram of an apparatus 200 to provide access in close proximity according to an embodiment. FIG. 2 shows the system 200 in cross section. Apparatus 200 solves the need in the art to place additional electronic medical diagnostic equipment or electronic medical monitoring equipment in close proximity to an MRI system.

Apparatus 200 includes the casing 102 having the inner bore 104. The inner bore 104 includes the two apertures 106 and 108.

Apparatus 200 also includes magnetic main coils that generate an asymmetric magnetic field. One embodiment of such magnetic main coils are magnetic main coils 202 that are asymmetrically shaped and that are asymmetrically positioned in the casing 102. Another embodiment of such magnetic main coils is magnetic main coils that have an asymmetric current (not shown). Apparatus 200 also includes asymmetric shield coils 204 that are one variant or embodiment of asymmetric shield coils 110 in FIG. 1.

The asymmetric position of the magnetic main coils 202, the asymmetric current in the magnetic main coils or the asymmetric position of the one or more magnetic shield coils 204 and 108 in the casing 102 generate an asymmetric stray magnetic 112 field during operation of the apparatus 200. The asymmetric magnetic stray field 112 provides a magnetic stray field that in which electronic medical diagnostic equipment or electronic medical monitoring equipment is operable in close proximity to the apparatus 200 on the side of the system in which the asymmetric magnetic stray field 112 does not extend as far from the apparatus 200 as the other side of system 200. Thus, apparatus 200 solves the need in the art to place additional electronic medical diagnostic equipment or electronic medical monitoring equipment in close proximity to apparatus 200.

In some embodiments of apparatus 200, the inner bore 104 is a stepped inner bore that has at least two portions, wherein the first portion 206 has a larger radius than the second portion 208.

In some embodiments of apparatus 200, an ellipsoidal magnetic field of view (FOV) 210 has dimensions of about 500 millimeters (mm) in the radial direction and 480 mm in the axial direction, a 5 gauss line of the asymmetric magnetic stray field 112 extends from the center of the magnetic FOV 210 to about 1.4 meters in a positive direction of a longitudinal Z axis 212, about 4.0 meters in a negative direction of the longitudinal Z axis 212, and about 2.5 meters in either direction from the Z axis along an R axis. The length of the asymmetric magnetic stray field 112 in the negative direction is about 2.5 meters more than the length of the stray field in the positive direction from the center of the FOV 210. The peak magnetic field in the winding is about 4.56 Teslas (T). Furthermore, the superconductor (SC) volume is about 102,966 cm$^3$, the total coil length is about 156 centimeters (cm).

Figure 3:
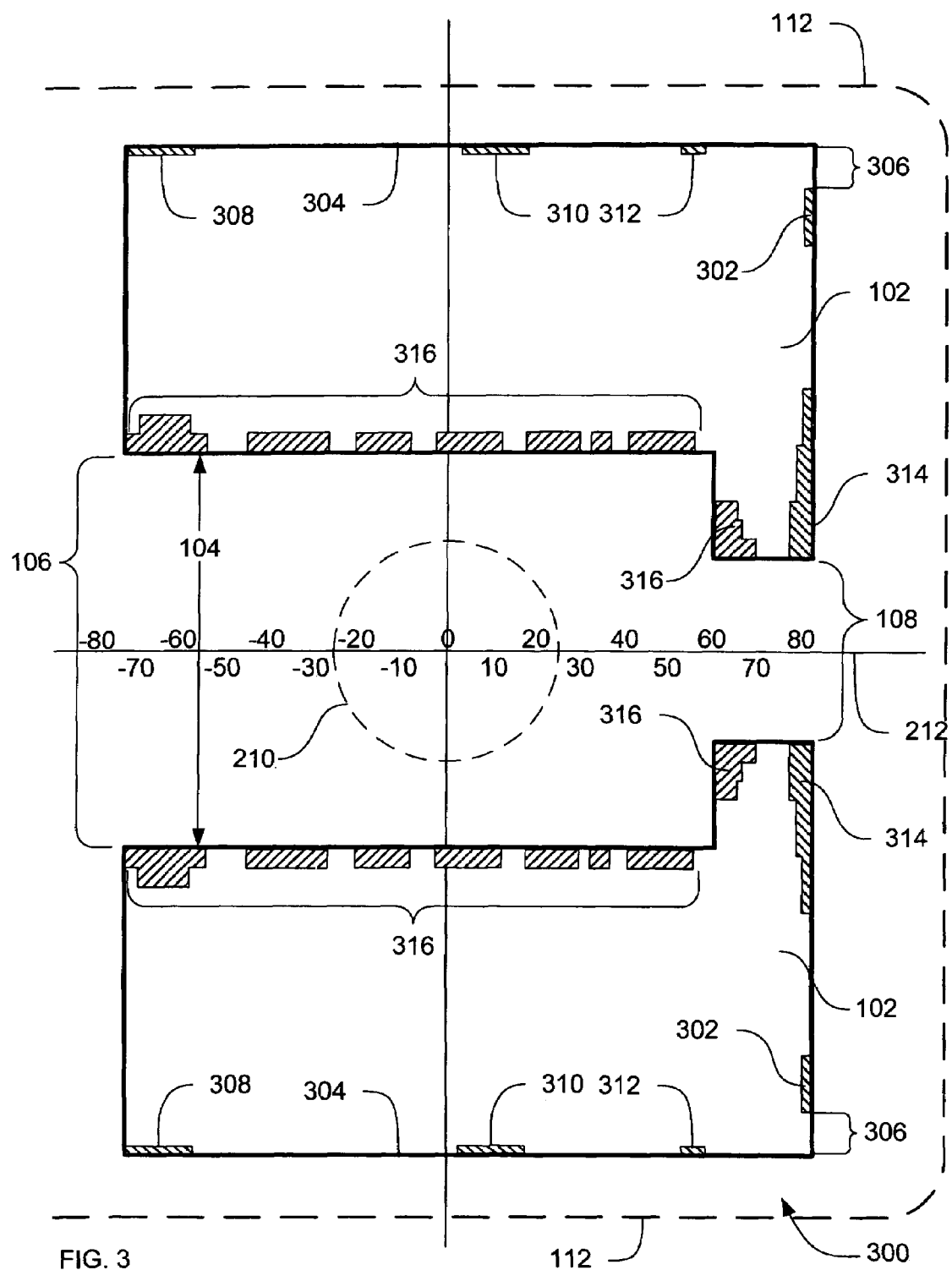
FIG. 3 is a diagram of apparatus having an embodiment of a magnetic shield coil.

FIG. 3 is a diagram of apparatus 300 having an embodiment of a magnetic shield coil. Apparatus 300 is one embodiment of apparatus 200 above.

Apparatus 300 includes an embodiment in which one of the one or more magnetic shield coils 110 of FIG. 1 and FIG. 2 is a magnetic shield coil 302 that is not positioned in close proximity to an enclosed inside surface 304 of the casing 102 that is opposite of the inner bore 104. More specifically, the magnetic shield coil 302 is positioned a distance 306 from the inside surface 304 of the casing 102 that is opposite of the inner bore 104, wherein the distance 306 provides more than a close proximity between the magnetic shield coil 302 and the inside surface 304 of the casing 102. In one embodiment, distance 306 is about 3 cm. The distance 306 between the magnetic shield coil 302 and the inside surface 304 of the casing 102 provides in part the asymmetrical magnetic stray field 112.

Some embodiments of apparatus 300 also include one or more magnetic shield coils positioned in close proximity to an inside surface 304 of the casing 102 that is opposite of the inner bore 104. The inside surface 304 of the casing 102 that is opposite of the inner bore 104 is also referred to as the outer diameter of the casing 102. Examples of such a magnetic shield coil include magnetic shield coils 308, 310 and 312.

Some embodiments of apparatus 300 also include one or more magnetic shield coils 314 asymmetrically shaped and asymmetrically positioned within casing 102 and positioned in close proximity to the inner diameter of the casing 102. Magnetic shield coils 314 are one embodiment of asymmetric shield coils 110 in FIG. 1.

In some embodiments of apparatus 300, an ellipsoidal magnetic FOV has dimensions of about 500 mm in the radial direction and 480 mm in the axial direction, a 5 gauss line of the asymmetric magnetic stray field 112 extends from the center of the magnetic FOV 210 to about 1.4 meters in a positive direction of a longitudinal Z axis 212, about 4.0 meters in a negative direction of the longitudinal Z axis 212, and about 2.5 meters in either direction from the Z axis along an R axis. The length of the asymmetric magnetic stray field 112 in the negative direction is about 2.6 meters more than the length of the stray field in the positive direction from the center of the magnetic FOV 210. The peak magnetic field in the winding is about 4.56 T. Furthermore, the SC volume is about 102,966 mm$^3$, the coil length is about 156 cm. A first negative coil uses about −432,679.6 ampere-turns (AT), has a R center of about 45.2 cm and a Z center of about 82.5 cm. A second negative coil uses about −21,122.95 AT, has a R center of about 83.5 cm and a Z center of about 83.0 cm.

Apparatus 300 also includes a particular embodiment of the main magnetic coils 202 of apparatus 200 in which the main magnetic coils 316 are shaped and positioned asymmetrically as shown in FIG. 3.

Figure 4:
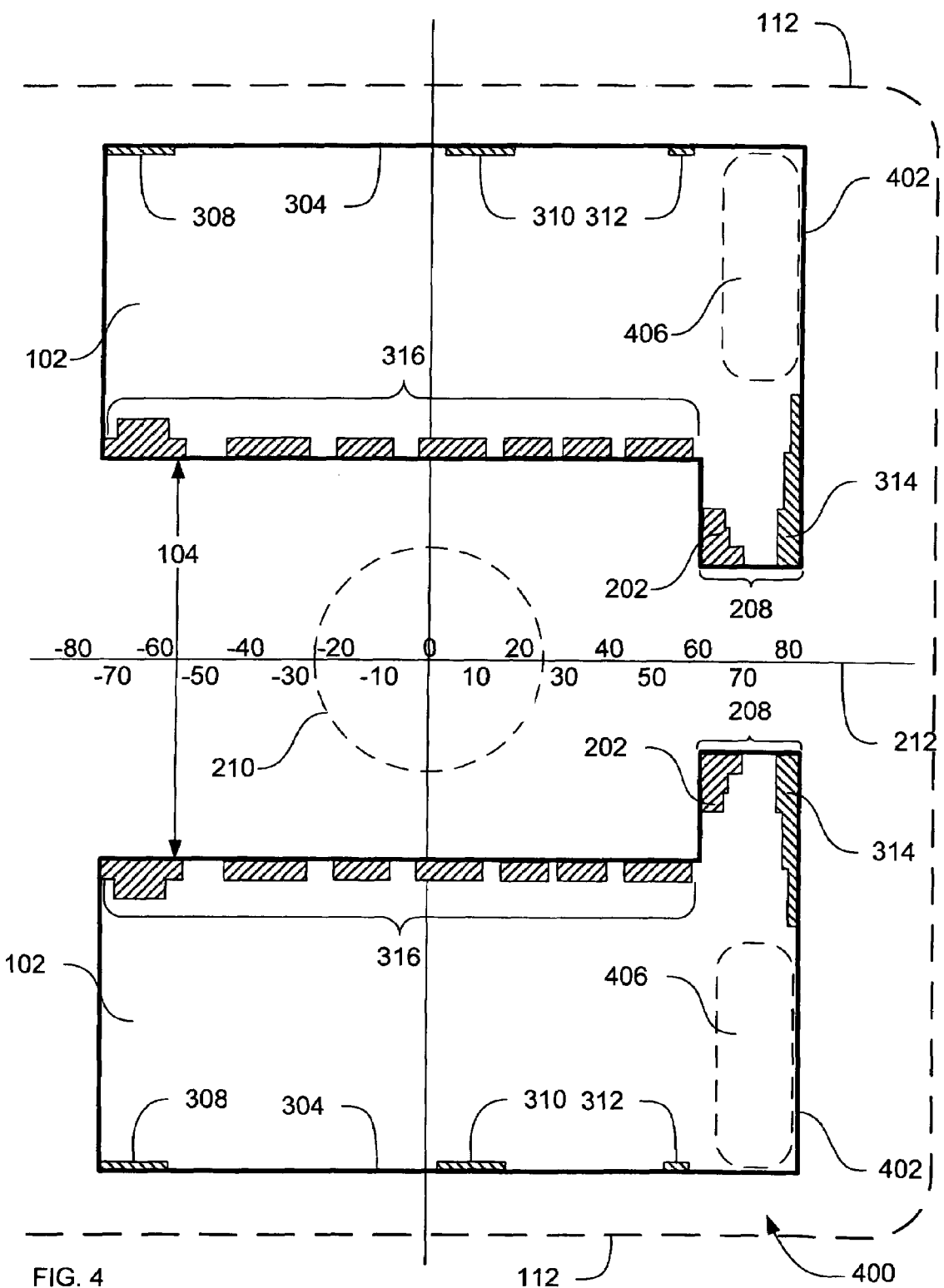
FIG. 4 is a diagram of apparatus according to an embodiment of magnetic shield coil having no outer diameter shield coil in an outer portion from the narrower diameter portion of a stepped bore.

FIG. 4 is a diagram of apparatus 400 according to an embodiment of magnetic shield coil having no outer diameter shield coil in an outer portion from the narrower diameter portion of a stepped bore.

Apparatus 400 includes an embodiment in the casing 102 that includes one or more magnetic shield coils 314 positioned along a face 402 of the casing and radially outward from the second portion 208 of the stepped bore having a narrower diameter in proximity to an inside surface 304 of the casing 102. The face 402 is aligned along a plane perpendicular to the longitudinal axis 212 and adjacent to the second portion 208. The one or more magnetic shield coils 314 are positioned in close proximity to the second portion 208. One example of the close proximity of the magnetic shield coils 314 to the second portion 208 in apparatus 400 is 30 centimeters or less, such as the magnetic shield coils 314 being adjacent to the second portion 208.

Noticeably absent from apparatus 400 is magnetic shield coil 302 in FIG. 3. Apparatus 400 excludes a magnetic shield coil positioned in a region 406 within the casing 102 along face 402 and beyond close proximity to the inside inner bore 104 of the casing 102. The absence of a magnetic shield coil in region 406 helps provide an asymmetric magnetic stray field 112 that provides placement and operation of electrical interventional equipment in close proximity to face 402 of apparatus 400 while reducing manufacturing complexity.

In some embodiments of apparatus 400, an ellipsoidal FOV 210 has dimensions of about 500 mm radially and 480 mm axially, a 5 gauss line of the asymmetric magnetic stray field 112 extends from the center of the magnetic FOV 210 to about 1.6 meters in a positive direction of a longitudinal Z axis 212, about 4.0 meters in a negative direction (not shown) of the longitudinal Z axis 212, and about 2.5 meters in either direction from the Z axis along an R axis. The length of the asymmetric magnetic stray field 112 in the negative direction is about 2.4 meters more than the length of the stray field in the positive direction from the center of the magnetic FOV 210. The peak magnetic field in the winding is about 4.37 Teslas (T). Furthermore, the superconductor (SC) volume is about 103,586 mm$^3$, the coil length is about 162 cm, a negative coil uses about −403,705 AT, has a R center of 45.3 cm and a Z center of about 85.7 cm.

Figure 5:
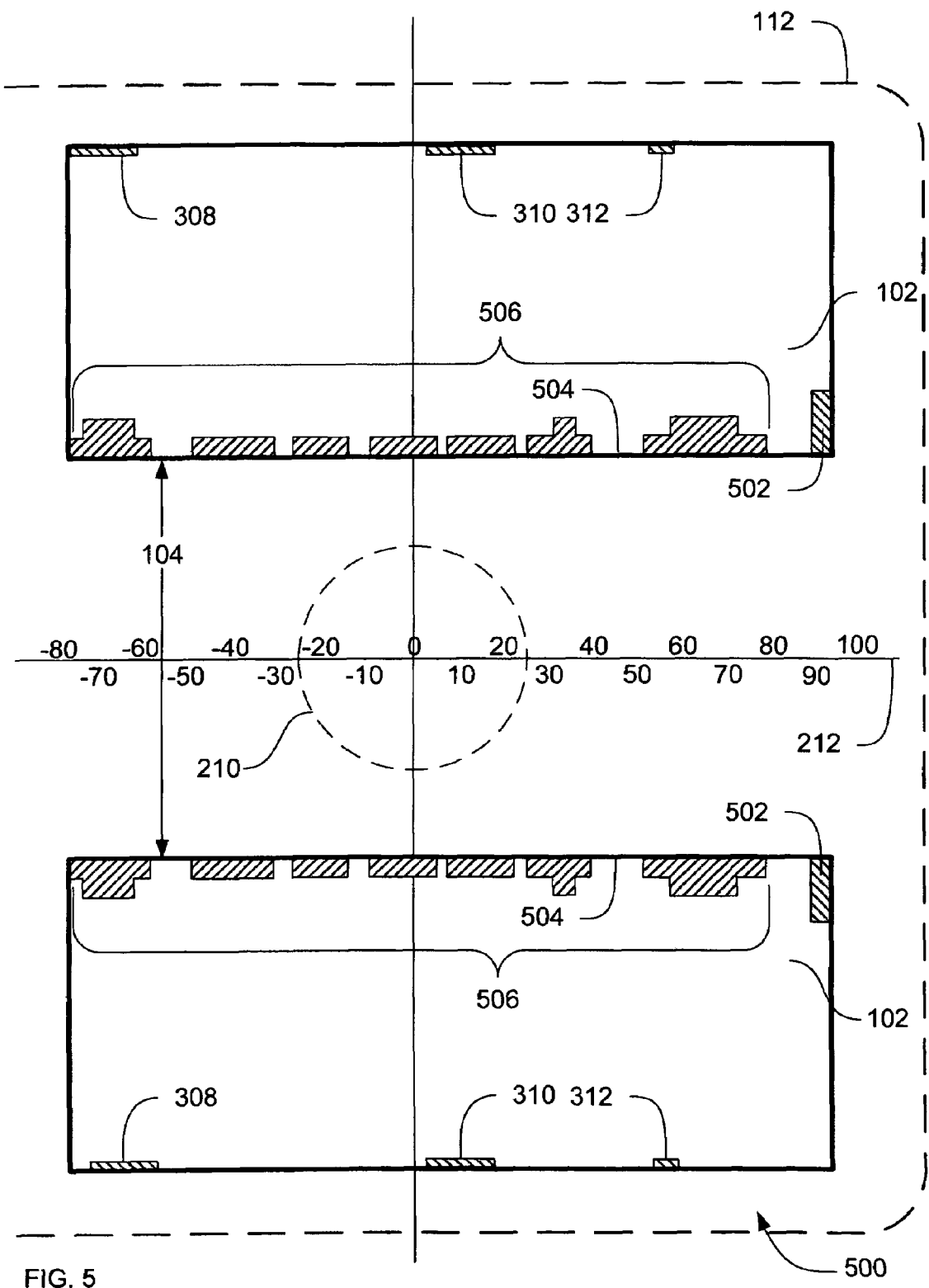
FIG. 5 is a diagram of apparatus according to an embodiment having a shield positioned along the inner diameter of the casing and a bore of a continuous diameter.

FIG. 5 is a diagram of apparatus 500 according to an embodiment having a shield positioned along the inner diameter of the casing and a bore of a continuous diameter.

Apparatus 500 includes an inner bore 104 having no stepped portions. Instead of stepped portions, the inner bore 104 has a diameter of continuous width throughout the entire length of the inner bore 104.

In addition, apparatus 500 has a magnetic shield coil 502 positioned close to the inside surface 504 of the casing 102 along the inner bore 104. Apparatus 500 also includes main magnetic coils 506 that are shaped and positioned asymmetrically as shown in FIG. 5.

In some embodiments of apparatus 500, an ellipsoidal magnetic FOV 210 has dimensions of about 500 mm in radial direction and 480 mm in axial direction, a 5 gauss line of the asymmetric magnetic stray field 112 extends from the center of the magnetic FOV 210 to about 1.8 meters in a positive direction of a longitudinal Z axis 212, about 4.0 meters in a negative direction of the longitudinal Z axis 212, and about 2.5 meters in either direction from the Z axis along an R axis. The length of the asymmetric magnetic stray field 112 in the negative direction is about 2.2 meters more than the length of the magnetic stray field in the positive direction from the center of the FOV 210. The peak magnetic field in a winding is about 4.3 T. Furthermore, the superconductor volume is about 113,774 $cm^3$, the coil length is about 172 cm, a negative coil uses about −414,647 AT, has a R center of 54 cm and a Z center of about 94.8 cm.

Figure 6:
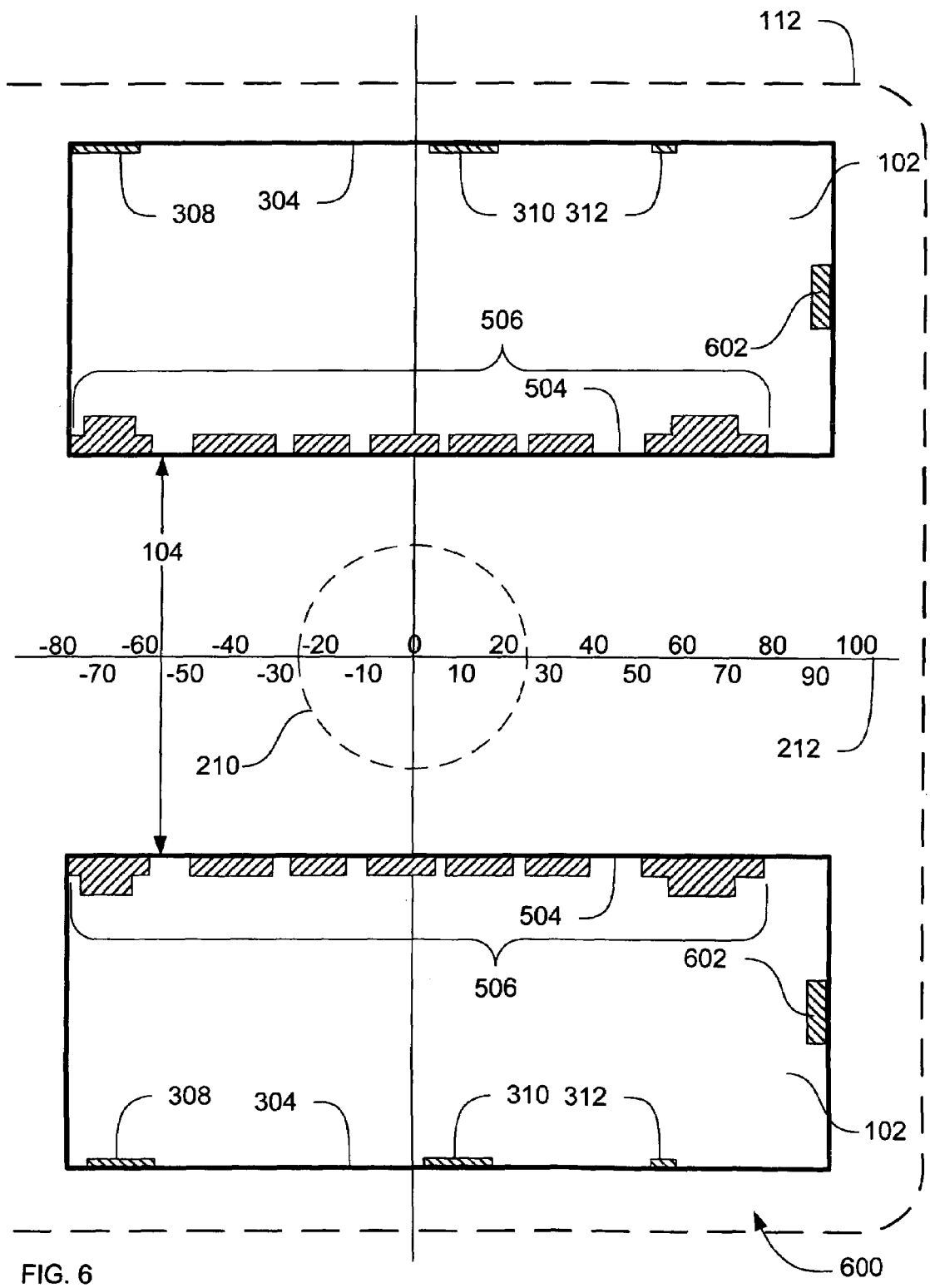
FIG. 6 is a diagram of apparatus according to an embodiment having a magnetic shield coil positioned between the inner diameter and the outer diameter of a casing.

FIG. 6 is a diagram of apparatus 600 according to an embodiment having a magnetic shield coil positioned between the inner diameter and the outer diameter of a casing.

Apparatus 600 includes an inner bore 104 having no stepped portions. Instead of stepped portions, the inner bore 104 has a diameter of continuous width throughout the entire length of the inner bore 104.

In addition, apparatus 600 has magnetic shield coils 602 that are not positioned in close proximity to the inside surface 504 of the casing 102 along the inner bore 104, and that are not positioned in close proximity to an inside surface 304 of the casing 102 that is opposite of the inner bore 104. Nonetheless, magnetic shield coils 602 are similar to shield coils 110 in FIG. 1 in that they are asymmetrically positioned within casing 102.

In some embodiments of apparatus 600, an ellipsoidal magnetic FOV has dimensions of about 500 mm in the radial direction and 480 mm in the axial direction, a 5 gauss line of the asymmetric magnetic stray field 112 extends from the center of the magnetic FOV 210 to about 2.1 meters in a positive direction of a longitudinal Z axis 212, about 4.0 meters in a negative direction of the longitudinal Z axis 212, and about 2.5 meters in either direction from the Z axis along an R axis. The length of the asymmetric magnetic stray field 112 in the negative direction is about 1.9 meters more than the length of the stray field in the positive direction from the center of the magnetic FOV. The peak magnetic field in a winding is about 4.3 T. Furthermore, the superconductor volume is about 113,774 $cm^3$, the total coil length is about 172 cm, a negative coil uses about −384,235 AT, has a R center of 66.2 cm and a Z center of about 94.8 cm.

Figure 7:
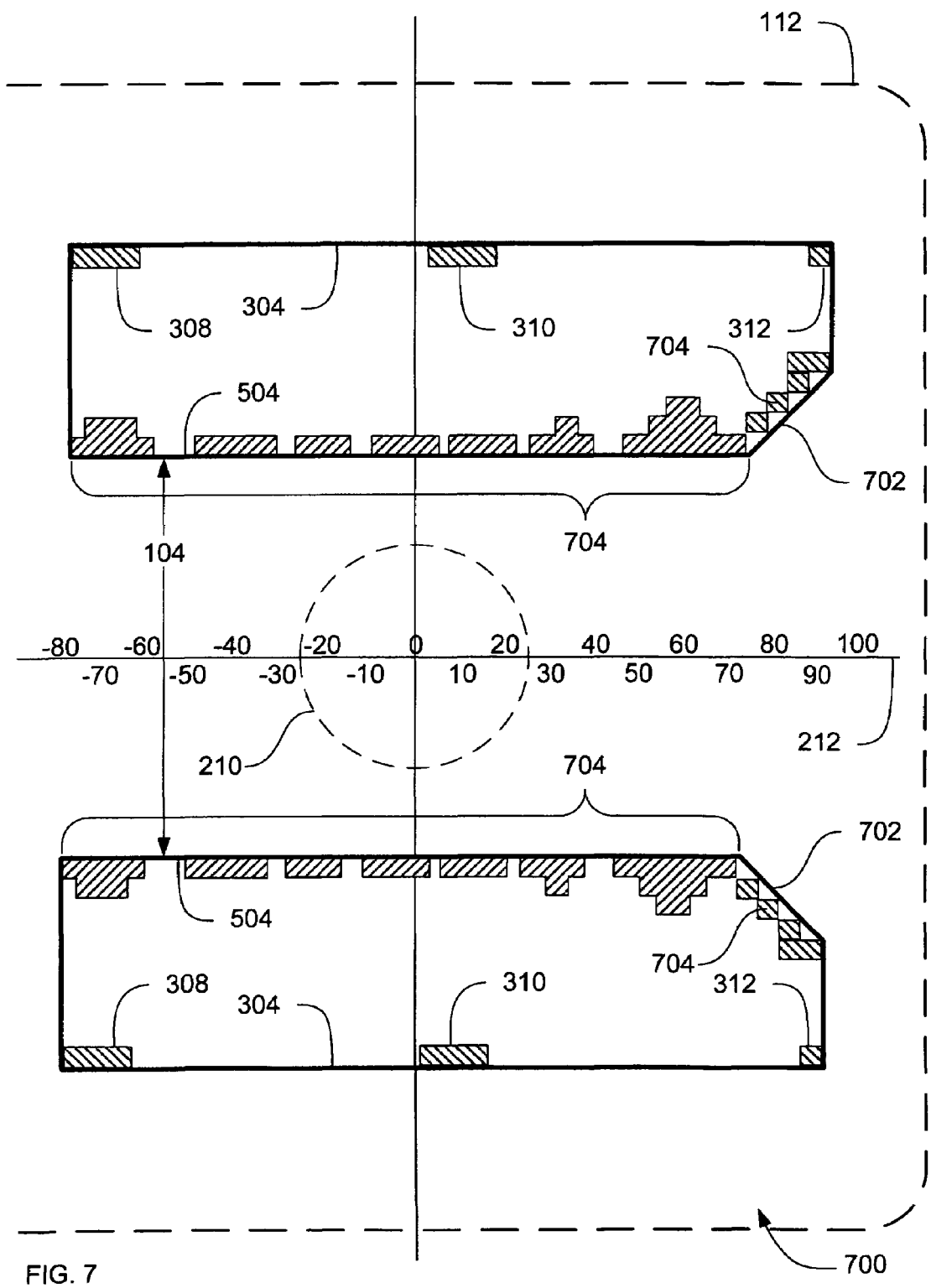
FIG. 7 is a diagram of apparatus according to an embodiment having a magnetic shield coil positioned between the inner diameter and the outer diameter of a flared casing.

FIG. 7 is a diagram of apparatus 700 according to an embodiment having a magnetic shield coil positioned between the inner diameter and the outer diameter of a flared casing.

Apparatus 700 includes an inner bore 104 having two apertures. Furthermore, the casing 102 has a flared end 702 towards one of the apertures of the inner bore 104.

In addition, apparatus 700 has one or more magnetic shield coils 704 that are not positioned in close proximity to the inside surface 504 of the casing 102 along the inner bore 104, and that is not positioned in close proximity to an inside surface 304 of the casing 102 that is opposite of the inner bore 104.

In some embodiments of apparatus 700, an ellipsoidal magnetic FOV has dimensions of about 500 mm in the radial direction and 480 mm in the axial direction, a 5 gauss line of the asymmetric magnetic stray field 112 extends from the center of the magnetic FOV 210 to about 2.1 meters in a positive direction of a longitudinal Z axis 212, about 4.0 meters in a negative direction of the longitudinal Z axis 212, and about 2.5 meters in either direction from the Z axis along an R axis. The length of the asymmetric magnetic stray field 112 in the negative direction is about 1.9 meters more than the length of the stray field in the positive direction from the center of the magnetic FOV. The peak magnetic field in a winding is about 4.5 T. Furthermore, the superconductor volume is about 119,050 $cm^3$, the coil length is about 172 cm, a negative coil uses about −505,135 AT, has a R center of 67.5 cm and a Z center of about 90.6 cm.

Methods of an Embodiment

In the previous section, apparatus of the operation of an embodiment was described. In this section, the particular methods performed by a processor of a magnetic resonance imaging (MRI) system, of such an embodiment are described by reference to a series of flowcharts.

Figure 8:
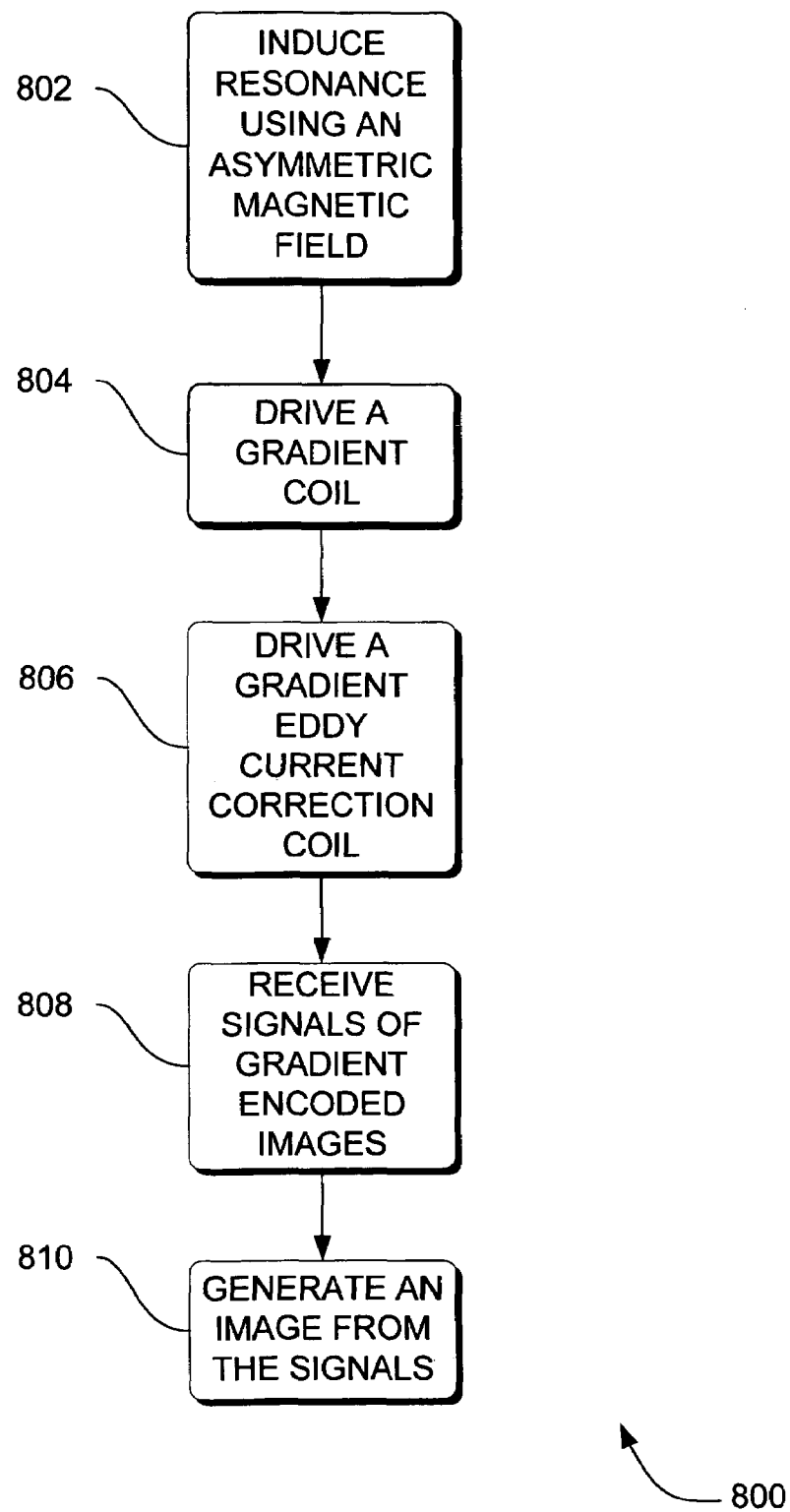
FIG. 8 is a flowchart of a method of generating an image from electromagnetic resonance induced by a magnet with an asymmetric stray field according to an embodiment.

FIG. 8 is a flowchart of a method 800 of generating an image from electromagnetic resonance induced by a magnet with an asymmetric stray field according to an embodiment.

Method 800 includes inducing 802 electromagnetic resonance in a subject, using an asymmetric magnet that produces an asymmetric stray field having a 5 gauss strength at about 0.5 meters from a magnetic shield coil. Method 800 includes driving 804 a gradient coil to spatially encode the image. Method 800 also includes driving 806 a gradient eddy current correction coil in the MRI. The coil compensates for the asymmetric eddy currents generated by the gradient coil in system 100, apparatus 200, 300, 400, 500, 600 and 700.

Method 800 further includes receiving 808 radio frequency signals of gradient encoded images with correction by the gradient eddy current correction coil. Method 800 also includes generating 810 an image from the radio frequency signals of gradient encoded images after correcting for asymmetric magnetic eddy currents.

Figure 9:
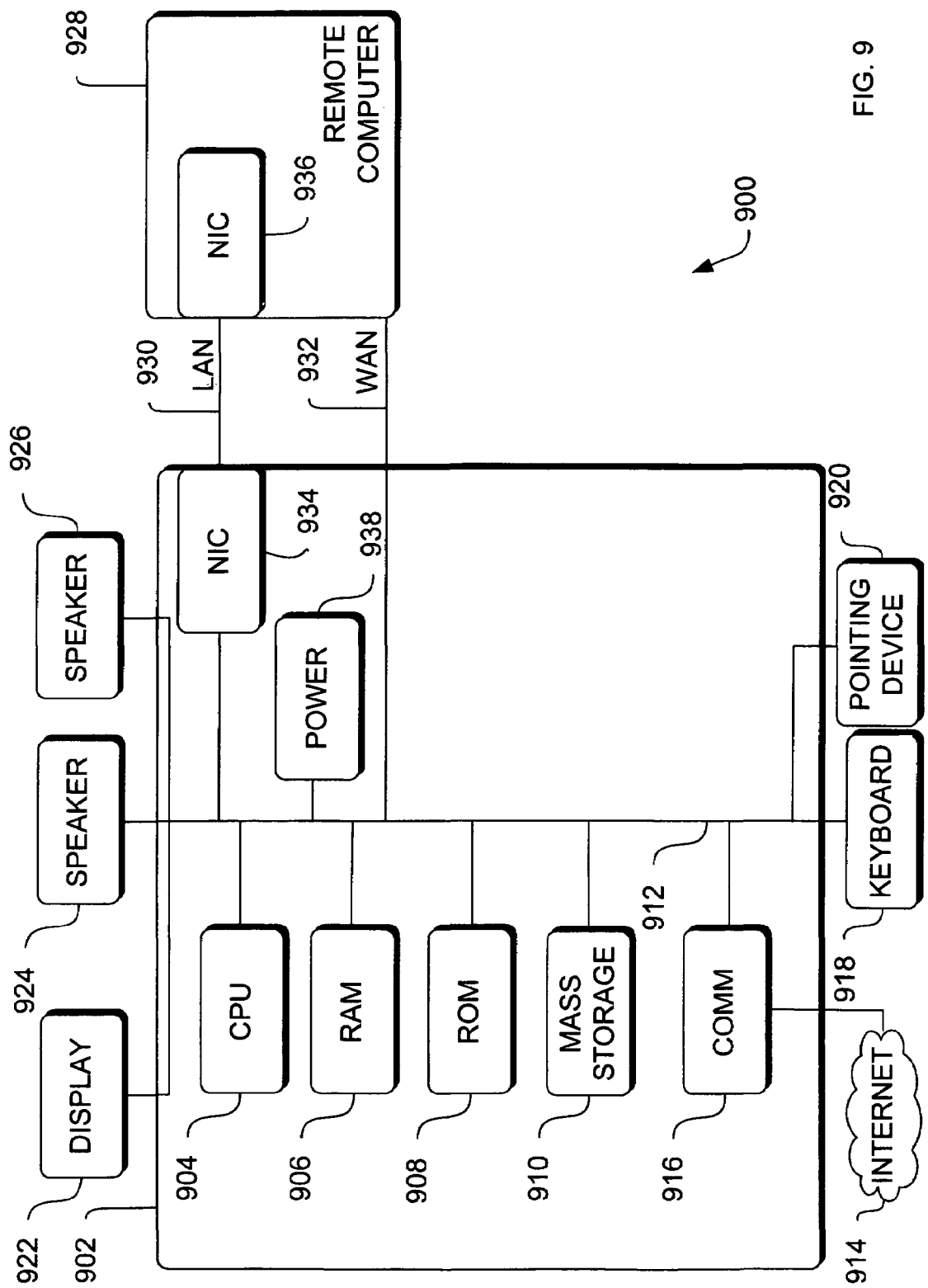
FIG. 9 is a block diagram of the hardware and operating environment in which different embodiments can be practiced.

In some embodiments, method 800 is implemented as a computer data signal embodied in a carrier wave, that represents a sequence of instructions which, when executed by a processor, such as processor 904 in FIG. 9, cause the processor to perform the respective method. In other embodiments, method 800 is implemented as a computer-accessible medium having executable instructions capable of directing a processor, such as processor 904 in FIG. 9, to perform the respective method. In varying embodiments, the medium is a magnetic medium, an electronic medium, or an optical medium.

Hardware and Operating Environment

FIG. 9 is a block diagram of the hardware and operating environment 900 in which different embodiments can be practiced. The description of FIG. 9 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 902 includes a processor 904, commercially available from Intel, Motorola, Cyrix and others. Computer 902 also includes random-access memory (RAM) 906, read-only memory (ROM) 908, and one or more mass storage devices 910, and a system bus 912, that operatively couples various system components to the processing unit 904. The memory 906, 908, and mass storage devices, 910, are types of computer-accessible media. Mass storage devices 910 are more specifically types of nonvolatile computer-accessible media and can include one or more hard disk drives, floppy disk drives, optical disk drives, and tape cartridge drives. The processor 904 executes computer programs stored on the computer-accessible media.

Computer 902 can be communicatively connected to the Internet 914 via a communication device 916. Internet 914 connectivity is well known within the art. In one embodiment, a communication device 916 is a modem that responds to communication drivers to connect to the Internet via what is known in the art as a "dial-up connection." In another embodiment, a communication device 916 is an Ethernet® or similar hardware network card connected to a local-area network (LAN) that itself is connected to the Internet via what is known in the art as a "direct connection" (e.g., T1 line, etc.).

A user enters commands and information into the computer 902 through input devices such as a keyboard 918 or a pointing device 920. The keyboard 918 permits entry of textual information into computer 902, as known within the art, and embodiments are not limited to any particular type of keyboard. Pointing device 920 permits the control of the screen pointer provided by a graphical user interface (GUI) of operating systems such as versions of Microsoft Windows®. Embodiments are not limited to any particular pointing device 920. Such pointing devices include mice, touch pads, trackballs, remote controls and point sticks. Other input devices (not shown) can include a microphone, joystick, game pad, satellite dish, scanner, or the like.

In some embodiments, computer 902 is operatively coupled to a display device 922. Display device 922 is connected to the system bus 912. Display device 922 permits the display of information, including computer, video and other information, for viewing by a user of the computer. Embodiments are not limited to any particular display device 922. Such display devices include cathode ray tube (CRT) displays (monitors), as well as flat panel displays such as liquid crystal displays (LCD's). In addition to a monitor, computers typically include other peripheral input/output devices such as printers (not shown). Speakers 924 and 926 provide audio output of signals. Speakers 924 and 926 are also connected to the system bus 912.

Computer 902 also includes an operating system (not shown) that is stored on the computer-accessible media RAM 906, ROM 908, and mass storage device 910, and is and executed by the processor 904. Examples of operating systems include Microsoft Windows®, Apple MacOS®, Linux®, UNIX®. Examples are not limited to any particular operating system, however, and the construction and use of such operating systems are well known within the art.

Embodiments of computer 902 are not limited to any type of computer 902. In varying embodiments, computer 902 comprises a PC-compatible computer, a MacOS®-compatible computer, a Linux®-compatible computer, or a UNIX®-compatible computer. The construction and operation of such computers are well known within the art.

Computer 902 can be operated using at least one operating system to provide a graphical user interface (GUI) including a user-controllable pointer. Computer 902 can have at least one web browser application program executing within at least one operating system, to permit users of computer 902 to access intranet or Internet world-wide-web pages as addressed by Universal Resource Locator (URL) addresses. Examples of browser application programs include Netscape Navigator® and Microsoft Internet Explorer®.

The computer 902 can operate in a networked environment using logical connections to one or more remote computers, such as remote computer 928. These logical connections are achieved by a communication device coupled to, or a part of, the computer 902. Embodiments are not limited to a particular type of communications device. The remote computer 928 can be another computer, a server, a router, a network PC, a client, a peer device or other common network node. The logical connections depicted in FIG. 9 include a local-area network (LAN) 930 and a wide-area network (WAN) 932. Such networking environments are commonplace in offices, enterprise-wide computer networks, intranets and the Internet.

When used in a LAN-networking environment, the computer 902 and remote computer 928 are connected to the local network 930 through network interfaces or adapters 934, which is one type of communications device 916. Remote computer 928 also includes a network device 936. When used in a conventional WAN-networking environment, the computer 902 and remote computer 928 communicate with a WAN 932 through modems (not shown). The modem, which can be internal or external, is connected to the system bus 912. In a networked environment, program modules depicted relative to the computer 902, or portions thereof, can be stored in the remote computer 928.

Computer 902 also includes power supply 938. Each power supply can be a battery.

CONCLUSION

An improved magnetic resonance imaging system has been described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in design methodology or any other methodology that provides the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future MRI devices, different magnetic coils, and new magnetic shields.

The terminology used in this application with respect to systems and apparatus is meant to include all MRI environments and alternate technologies which provide the same functionality as described herein.

We claim:

1. A magnetic resonance imaging apparatus to allow access in close proximity to the apparatus, the apparatus comprising:
   a casing having an inner bore, the inner bore having two apertures; and
   at least one magnetic shield coil positioned asymmetrically in the casing, the magnetic shield coil positioned in close proximity to one of the two apertures and the magnetic shield coil positioned in close proximity to the inner bore.

2. The magnetic resonance imaging apparatus of claim 1, wherein the system generates an asymmetric magnetic stray field having a 5 gauss strength at about 0.5 meters from where the at least one magnetic shield coil is positioned.

3. The magnetic resonance imaging apparatus of claim 1, wherein the apparatus further comprises:
   a magnetic shield coil not positioned in close proximity to an inside surface of the casing that is opposite of the inner bore.

4. The magnetic resonance imaging apparatus of claim 1, wherein the apparatus further comprises:
   another magnetic shield coil positioned in close proximity to an inside surface of the casing that is opposite of the inner bore.

5. The magnetic resonance imaging apparatus of claim 1, wherein the inner bore defines an inner diameter of the casing, the inner diameter having at least two portions, wherein the first portion has a larger radius than the second portion.

6. The magnetic resonance imaging apparatus of claim 1, wherein the magnetic shield coil positioned in close proximity to one of the two the apertures and the magnetic shield coil positioned in close proximity to the inner bore further comprises:
   the magnetic shield coil positioned adjacent to one of the two the apertures; and
   the magnetic shield coil positioned adjacent to the inner bore.

7. A magnetic resonance imaging apparatus to allow access in close proximity to the apparatus, the apparatus comprising:
   a casing having an inner bore, the inner bore having two apertures;
   a plurality of magnetic main coils operable to generate an asymmetrical magnetic field; and
   at least one magnetic shield coil positioned asymmetrically in the casing, positioned in close proximity to one of the two apertures and positioned in close proximity to the inner bore;
   wherein the inner bore defines an inner diameter of the casing, the inner diameter having at least two portions, wherein the first portion has a larger radius than the second portion.

8. The magnetic resonance imaging apparatus of claim 7, wherein the apparatus further comprises:
   a magnetic shield coil not positioned in close proximity to an inside surface of the casing that is opposite of the inner bore.

9. The magnetic resonance imaging apparatus of claim 7, wherein the apparatus further comprises:
   a magnetic shield coil positioned in close proximity to an inside surface of the casing that is opposite of the inner bore.

10. A magnetic resonance imaging system to allow access in close proximity to the apparatus, the apparatus comprising:
    a casing having an inner bore, the inner bore having two apertures;
    a plurality of magnetic main coils positioned asymmetrically in the casing; and
    at least one magnetic shield coil positioned asymmetrically in the casing, positioned in close proximity to one of the two apertures and positioned in close proximity to the inner bore;
    wherein no magnetic shield coil is positioned in close proximity to an inside surface of the casing that is opposite of the inner bore.

11. The system of claim 10, wherein the apparatus further comprises:
    another magnetic shield coil positioned in close proximity to an inside surface of the casing that is opposite of the inner bore 12. The system of claim 10, wherein the inner bore defines an inner diameter of the casing, the inner diameter having at least two portions, wherein the first portion has a larger radius than the second portion.

13. An apparatus to image a subject and allow operation of electrically operated equipment within close proximity of the apparatus, the apparatus comprising:
    a casing having an enclosed inside surface and an exterior surface, the casing further having a longitudinal axis and an inner bore centered around the longitudinal axis, wherein the inner bore defines an inner diameter of the casing, the inner diameter having at least two portions, wherein the first portion has a larger radius than the second portion, the casing further comprising a face along a plane perpendicular to the longitudinal axis and adjacent to the second portion; and
    at least one magnetic shield coil positioned along the face of the casing and radially outward from the second portion of the inner diameter, the at least one magnetic shield coil further positioned in close proximity to the inside surface of the casing,
    wherein the apparatus does not comprise a magnetic shield coil positioned along the face of the casing and beyond close proximity to the inside inner bore of the casing.

14. The apparatus of claim 13, wherein the at least one magnetic shield coil further comprises:
    being positioned in close proximity to the second portion.

15. The apparatus of claim 13, wherein the apparatus further comprises:
    another magnetic shield coil positioned in close proximity to an inside surface of the casing that is opposite of the inner bore.

16. A magnetic resonance imaging apparatus to allow access in close proximity to the apparatus, the apparatus comprising:
    a casing having an inner bore, the inner bore having a diameter of continuous width throughout the entire length of the inner bore; and
    a magnetic shield coil positioned close to an inside surface of the casing along the inner bore.

17. The magnetic resonance imaging apparatus of claim 16, wherein the magnetic shield coil further comprises:
    a magnetic shield coil not positioned in close proximity to an inside surface of the casing that is opposite of the inner bore.

18. The magnetic resonance imaging apparatus of claim 16, wherein the magnetic shield coil further comprises:
    being positioned in close proximity to one of the two apertures.

19. A magnetic resonance imaging apparatus to allow access in close proximity to the apparatus, the apparatus comprising:
- a casing having an inner bore, the inner bore having a diameter of continuous width throughout the entire length of the inner bore;
- a magnetic shield coil not positioned in close proximity to an inside surface of the casing along the inner bore; and
- the magnetic shield coil not positioned in close proximity to an inside surface of the casing that is opposite of the inner bore.

20. The magnetic resonance imaging apparatus of claim 19, wherein the magnetic shield coil further comprises:
- being positioned in close proximity to one of the two apertures.

21. A magnetic resonance imaging apparatus to allow access in close proximity to the apparatus, the apparatus comprising:
- a casing having an inner bore, the inner bore being flared toward an end;
- a magnetic shield coil not positioned in close proximity to an inside surface of the casing along the inner bore; and
- the magnetic shield coil not positioned in close proximity to an inside surface of the casing that is opposite of the inner bore.

22. The magnetic resonance imaging apparatus of claim 21, wherein the magnetic shield coil further comprises:
- being positioned in close proximity to the flared end.

* * * * *